(12) United States Patent
Nitzan et al.

(10) Patent No.: US 9,707,382 B2
(45) Date of Patent: *Jul. 18, 2017

(54) DEVICE AND METHOD FOR REGULATING PRESSURE IN A HEART CHAMBER

(71) Applicant: V-WAVE LTD., Or Akiva (IL)

(72) Inventors: Yaacov Nitzan, Herzlia (IL); Boaz Harari, Tel-Aviv (IL); Ascher Shmulewitz, Tel-Aviv (IL); Tovy Sivan, Kfar-Saba (IL)

(73) Assignee: V-Wave Ltd., Caesarea (IL)

( * ) Notice: Subject to any disclaimer, the term of this patent is extended or adjusted under 35 U.S.C. 154(b) by 784 days.

This patent is subject to a terminal disclaimer.

(21) Appl. No.: 14/227,982

(22) Filed: Mar. 27, 2014

(65) Prior Publication Data

US 2014/0213959 A1 Jul. 31, 2014

Related U.S. Application Data

(63) Continuation of application No. 13/108,880, filed on May 16, 2011, now Pat. No. 8,696,611, which is a
(Continued)

(51) Int. Cl.
*A61M 5/00* (2006.01)
*A61M 27/00* (2006.01)
*A61F 2/24* (2006.01)

(52) U.S. Cl.
CPC ......... *A61M 27/002* (2013.01); *A61F 2/2412* (2013.01); *A61F 2/2418* (2013.01);
(Continued)

(58) Field of Classification Search
CPC . A61M 27/002; A61M 27/006; A61F 2/2412; A61F 2/2418; A61F 2220/0058;
(Continued)

(56) References Cited

U.S. PATENT DOCUMENTS 3,874,388 A 4/1975 King et al.
4,601,309 A 7/1986 Chang
(Continued)

FOREIGN PATENT DOCUMENTS

FR 2827153 1/2003
WO WO-99/60941 A1 12/1999
(Continued)

OTHER PUBLICATIONS

Extended European Search Report dated Jan. 8, 2015 in EP Patent Appl No. 10772089.8.
(Continued)

*Primary Examiner* — Tatyana Zalukaeva
*Assistant Examiner* — Ariana Zimbouski
(74) *Attorney, Agent, or Firm* — Foley & Lardner LLP; Christopher C. Bolten; Nicola A. Pisano

(57) ABSTRACT

A device for regulating blood pressure in a heart chamber is provided. The device includes a shunt positionable within a septum of the heart. The shunt is designed for enabling blood flow between a left heart chamber and a right heart chamber, wherein the flow rate capacity of the device is mostly a function of pressure in the left heart chamber.

22 Claims, 9 Drawing Sheets

Related U.S. Application Data continuation of application No. PCT/IL2010/000354, filed on May 4, 2010.

(60) Provisional application No. 61/175,073, filed on May 4, 2009, provisional application No. 61/240,667, filed on Sep. 9, 2009.

(52) U.S. Cl.
CPC ..... *A61M 27/006* (2013.01); *A61F 2002/249* (2013.01); *A61F 2220/0058* (2013.01); *A61F 2220/0066* (2013.01); *A61F 2230/0013* (2013.01); *A61F 2230/0078* (2013.01)

(58) Field of Classification Search
CPC ...... A61F 2220/0066; A61F 2230/0013; A61F 2230/0078; A61F 2002/249
See application file for complete search history.

(56) References Cited

U.S. PATENT DOCUMENTS

| | | | |
|---|---|---|---|
| 4,662,355 A | 5/1987 | Pieronne et al. |
| 4,705,507 A | 11/1987 | Boyles |
| 4,836,204 A | 6/1989 | Landymore et al. |
| 4,979,955 A | 12/1990 | Smith |
| 4,995,857 A | 2/1991 | Arnold |
| 5,186,431 A | 2/1993 | Tamari |
| 5,267,940 A | 12/1993 | Moulder |
| 5,290,227 A | 3/1994 | Pasque |
| 5,312,341 A | 5/1994 | Turi |
| 5,326,374 A | 7/1994 | Ilbawi et al. |
| 5,332,402 A | 7/1994 | Teitelbaum |
| 5,334,217 A | 8/1994 | Das |
| 5,409,019 A | 4/1995 | Wilk |
| 5,429,144 A | 7/1995 | Wilk |
| 5,500,015 A | 3/1996 | Deac |
| 5,531,759 A | 7/1996 | Kensey et al. |
| 5,556,386 A | 9/1996 | Todd |
| 5,584,803 A | 12/1996 | Stevens et al. |
| 5,597,377 A | 1/1997 | Aldea |
| 5,645,559 A | 7/1997 | Hachtman et al. |
| 5,655,548 A | 8/1997 | Nelson et al. |
| 5,662,711 A | 9/1997 | Douglas |
| 5,702,412 A | 12/1997 | Popov et al. |
| 5,725,552 A | 3/1998 | Kotula et al. |
| 5,795,307 A | 8/1998 | Krueger |
| 5,810,836 A | 9/1998 | Hussein et al. |
| 5,824,071 A | 10/1998 | Nelson et al. |
| 5,916,193 A | 6/1999 | Stevens et al. |
| 5,941,850 A | 8/1999 | Shah et al. |
| 5,957,949 A | 9/1999 | Leonhardt et al. |
| 6,039,759 A | 3/2000 | Carpentier et al. |
| 6,120,534 A | 9/2000 | Ruiz |
| 6,126,686 A | 10/2000 | Badylak et al. |
| 6,165,188 A | 12/2000 | Saadat et al. |
| 6,210,318 B1 | 4/2001 | Lederman |
| 6,217,541 B1 | 4/2001 | Yu |
| 6,242,762 B1 | 6/2001 | Brown et al. |
| 6,254,564 B1 | 7/2001 | Wilk et al. |
| 6,260,552 B1 | 7/2001 | Mortier et al. |
| 6,270,526 B1 | 8/2001 | Cox |
| 6,277,078 B1 | 8/2001 | Porat et al. |
| 6,302,892 B1 | 10/2001 | Wilk |
| 6,328,699 B1 | 12/2001 | Eigler et al. |
| 6,344,022 B1 | 2/2002 | Jarvik |
| 6,358,277 B1 | 3/2002 | Duran |
| 6,406,422 B1 | 6/2002 | Landesberg |
| 6,447,539 B1 | 9/2002 | Nelson et al. |
| 6,451,051 B2 | 9/2002 | Drasler et al. |
| 6,458,153 B1 | 10/2002 | Bailey et al. |
| 6,468,303 B1 | 10/2002 | Amplatz et al. |
| 6,478,776 B1 | 11/2002 | Rosenman et al. |
| 6,491,705 B2 | 12/2002 | Gifford et al. |
| 6,527,698 B1 | 3/2003 | Kung et al. |
| 6,544,208 B2 | 4/2003 | Ethier et al. |
| 6,562,066 B1 | 5/2003 | Martin |
| 6,572,652 B2 | 6/2003 | Shaknovich |
| 6,589,198 B1 | 7/2003 | Soltanpour et al. |
| 6,632,169 B2 | 10/2003 | Korakianitis et al. |
| 6,638,303 B1 | 10/2003 | Campbell |
| 6,641,610 B2 | 11/2003 | Wolf et al. |
| 6,685,664 B2 | 2/2004 | Levin et al. |
| 6,712,836 B1 | 3/2004 | Berg et al. |
| 7,001,409 B2 | 2/2006 | Amplatz |
| 7,149,587 B2 | 12/2006 | Wardle et al. |
| 7,294,115 B1 | 11/2007 | Wilk |
| 7,794,473 B2 | 9/2010 | Tessmer et al. |
| 7,988,724 B2 | 8/2011 | Salahieh et al. |
| 8,016,877 B2 | 9/2011 | Seguin et al. |
| 8,043,360 B2 | 10/2011 | Mcnamara et al. |
| 8,070,708 B2 | 12/2011 | Rottenberg et al. |
| 8,091,556 B2 | 1/2012 | Keren et al. |
| 8,096,959 B2 | 1/2012 | Stewart et al. |
| 8,147,545 B2 | 4/2012 | Avior |
| 8,157,860 B2 | 4/2012 | Mcnamara et al. |
| 8,235,916 B2 | 8/2012 | Whiting et al. |
| 8,235,933 B2 | 8/2012 | Keren et al. |
| 8,246,677 B2 | 8/2012 | Ryan |
| 8,303,511 B2 | 11/2012 | Eigler et al. |
| 8,328,751 B2 | 12/2012 | Keren et al. |
| 8,348,996 B2 | 1/2013 | Tuval et al. |
| 8,398,708 B2 | 3/2013 | Meiri et al. |
| 8,460,366 B2 | 6/2013 | Rowe |
| 8,579,966 B2 | 11/2013 | Seguin et al. |
| 8,597,225 B2 | 12/2013 | Kapadia |
| 8,696,611 B2 * | 4/2014 | Nitzan ................. A61F 2/2418 604/8 |
| 9,034,034 B2 | 5/2015 | Nitzan et al. |
| 2002/0165606 A1 | 11/2002 | Wolf et al. |
| 2002/0169371 A1 | 11/2002 | Gilderdale |
| 2002/0169377 A1 | 11/2002 | Khairkhahan et al. |
| 2002/0173742 A1 | 11/2002 | Keren et al. |
| 2003/0100920 A1 | 5/2003 | Akin et al. |
| 2003/0125798 A1 | 7/2003 | Martin |
| 2003/0136417 A1 | 7/2003 | Fonseca et al. |
| 2003/0176914 A1 * | 9/2003 | Rabkin ................... A61F 2/91 623/1.15 |
| 2003/0209835 A1 | 11/2003 | Chun et al. |
| 2003/0216679 A1 | 11/2003 | Wolf et al. |
| 2004/0010219 A1 | 1/2004 | McCusker et al. |
| 2004/0016514 A1 | 1/2004 | Nien |
| 2004/0077988 A1 | 4/2004 | Tweden et al. |
| 2004/0088045 A1 | 5/2004 | Cox |
| 2004/0093075 A1 | 5/2004 | Kuehne |
| 2004/0102797 A1 | 5/2004 | Golden et al. |
| 2004/0138743 A1 | 7/2004 | Myers et al. |
| 2004/0147869 A1 | 7/2004 | Wolf et al. |
| 2004/0147871 A1 | 7/2004 | Burnett |
| 2004/0147886 A1 | 7/2004 | Bonni |
| 2004/0162514 A1 | 8/2004 | Alferness et al. |
| 2004/0193261 A1 | 9/2004 | Berreklouw |
| 2004/0210190 A1 | 10/2004 | Kohler et al. |
| 2004/0210307 A1 * | 10/2004 | Khairkhahan ........ A61F 2/2403 623/2.18 |
| 2005/0033351 A1 | 2/2005 | Newton |
| 2005/0065589 A1 | 3/2005 | Schneider et al. |
| 2005/0137682 A1 * | 6/2005 | Justino ................. A61F 2/2412 623/1.24 |
| 2005/0148925 A1 | 7/2005 | Rottenberg et al. |
| 2005/0165344 A1 | 7/2005 | Dobak et al. |
| 2005/0182486 A1 | 8/2005 | Gabbay |
| 2005/0283231 A1 | 12/2005 | Haug et al. |
| 2006/0025857 A1 | 2/2006 | Bergheim et al. |
| 2006/0111660 A1 | 5/2006 | Wolf et al. |
| 2006/0116710 A1 | 6/2006 | Corcoran et al. |
| 2006/0122647 A1 | 6/2006 | Callaghan et al. |
| 2006/0167541 A1 | 7/2006 | Lattouf |
| 2006/0212110 A1 | 9/2006 | Osborne et al. |
| 2006/0282157 A1 | 12/2006 | Hill et al. |
| 2007/0010852 A1 | 1/2007 | Blaeser et al. |
| 2007/0043435 A1 | 2/2007 | Seguin et al. |
| 2007/0213813 A1 | 9/2007 | Von Segesser et al. |
| 2007/0282157 A1 | 12/2007 | Rottenberg et al. |

(56) References Cited

U.S. PATENT DOCUMENTS

| | | | |
|---|---|---|---|
| 2007/0299384 A1 | 12/2007 | Faul et al. | |
| 2008/0086205 A1 | 4/2008 | Gordy et al. | |
| 2008/0262602 A1 | 10/2008 | Wilk et al. | |
| 2009/0054976 A1 | 2/2009 | Tuval et al. | |
| 2009/0125104 A1 | 5/2009 | Hoffman | |
| 2009/0276040 A1 | 11/2009 | Rowe et al. | |
| 2010/0004740 A1* | 1/2010 | Seguin | A61F 2/2412 623/2.18 |
| 2010/0057192 A1 | 3/2010 | Celermajer | |
| 2010/0249909 A1 | 9/2010 | McNamara et al. | |
| 2010/0249910 A1 | 9/2010 | McNamara et al. | |
| 2010/0256548 A1 | 10/2010 | McNamara et al. | |
| 2010/0256753 A1 | 10/2010 | McNamara et al. | |
| 2010/0298755 A1 | 11/2010 | McNamara et al. | |
| 2011/0022157 A1 | 1/2011 | Essinger et al. | |
| 2011/0054515 A1 | 3/2011 | Bridgeman et al. | |
| 2011/0071623 A1 | 3/2011 | Finch et al. | |
| 2011/0071624 A1 | 3/2011 | Finch et al. | |
| 2011/0218479 A1 | 9/2011 | Rottenberg et al. | |
| 2011/0218480 A1 | 9/2011 | Rottenberg et al. | |
| 2011/0218481 A1 | 9/2011 | Rottenberg et al. | |
| 2011/0306916 A1 | 12/2011 | Nitzan et al. | |
| 2012/0071918 A1 | 3/2012 | Amin et al. | |
| 2012/0165928 A1 | 6/2012 | Nitzan et al. | |
| 2012/0271398 A1 | 10/2012 | Essinger et al. | |
| 2013/0030521 A1 | 1/2013 | Nitzan et al. | |
| 2013/0197423 A1 | 8/2013 | Keren et al. | |
| 2014/0128795 A1 | 5/2014 | Keren et al. | |
| 2014/0128796 A1 | 5/2014 | Keren et al. | |
| 2014/0163449 A1 | 6/2014 | Rottenberg et al. | |
| 2014/0213959 A1 | 7/2014 | Nitzan et al. | |
| 2014/0350565 A1 | 11/2014 | Yacoby et al. | |
| 2015/0039084 A1 | 2/2015 | Levi et al. | |
| 2015/0245908 A1 | 9/2015 | Nitzan et al. | |

FOREIGN PATENT DOCUMENTS

| | | |
|---|---|---|
| WO | WO-2005/027752 A1 | 3/2005 |
| WO | WO-2005/074367 A1 | 8/2005 |
| WO | WO-2006/127765 A1 | 11/2006 |
| WO | WO-2007/083288 A2 | 7/2007 |
| WO | WO-2008/055301 A1 | 5/2008 |
| WO | WO-2009/029261 A1 | 3/2009 |
| WO | WO-2010/128501 A1 | 11/2010 |

OTHER PUBLICATIONS

ISR & Written Opinion dated Feb. 16, 2015 in Int'l PCT Patent Appl Serial No. PCT/IB2014/001771.
Ando et al., "Left vetricular decompression through a patent foramen ovale in a patient with hypertrophic cardiomyopathy: A case report," Cardiovascular Ultrasound, (2004), 2:1-7.
Article 34 Amendments dated May 28, 2013 in related International PCT Patent Appl No. PCT/IB2012/001859.
Article 34 Amendments dated Nov. 27, 2012, as filed in related Int'l PCT Application No. PCT/IS2011/000958.
Bristow et al., "Improvement in cardiac myocite function by biological effects of medical therapy: A new concept in the treatment of heart failure," European Heart Journal, (1995), 16(Suppl.F):20-31.
Case et al., "Relief of High Left-Atrial Pressure in Left-Ventricular Failure," Lancet, (Oct. 17, 1964), pp. 841-842.
Coats et al., "Controlled trial of physical training in chronic heart failure: Exercise preformance, hemodynamics, ventilation, and autonomic function," Circulation, (1992), 85:2119-2131.
Davies et al., "Reduced contraction and altered frequency response of isolated ventricular myocytes from patients with heart failure," Circulation, (1995), 92:2540-2549.
Ennezat et al., "An unusual case of low-flow, low gradient severe aortic stenosis: Left-to-right shunt due to atrial septal defect," Cardiology, (2009), 113(2):146-148.

Ewert et al., "Acute left heart failure after interventional occlusion of an atrial septal defect," Z. Kardiol., (May 2001), 90(5):362-366.
Ewert et al., "Masked left ventricular restriction in elderly patients with atrial septal defects: A contraindication for closure?" Catheterization and Cardiovascular Interventions, (2001), 52:177-180.
Geiran et al., "Changes in cardiac dynamics by opening an interventricular shunt in dogs," J. Surg. Res., (Jan. 1990), 48(1):6-12.
Gelernter-Yaniv et al., "Transcatheter closure of left-to-right interatrial shunts to resolve hypoxemia," Congenit. Heart Dis., (Jan. 2008), 31(1):47-53.
Gewillig et al., "Creation with a stent of an unrestrictive lasting atrial communication," Cardio. Young, (2002), 12(4):404-407.
International Preliminary Report on Patentability dated Nov. 14, 2013 in related International PCT Patent Appl No. PCT/IB2012/001859.
International Search Report for PCT/IL2005/000131 dated Apr. 7, 2008, (3 pages).
International Search Report for PCT/IL2010/000354 dated Aug. 25, 2010 (1 pg).
Int'l Preliminary Report on Patentability dated Mar. 5, 2013, in related Int'l PCT Patent Appl No. PCT/IL2011/000958.
Kramer et al., "Controlled study of captopril in chronic heart failure: A rest and exercise hemodynamic study," Circulation, (1983), 67(4):807-816.
Lai et al., "Bidirectional shunt through a residual atrial septal defect after percutaneous transvenous mitral commissurotomy," Cardiology, (1993), 83(3):205-207.
Lemmer et al., "Surgical implications of atrial septal defect complicating aortic balloon valvuloplasty," Ann. thorac. Surg., (Aug. 1989), 48(2):295-297.
Merriam-Webster "Definition of 'Chamber'," OnLine Dictionary 2004, Abstract.
Schubert et al., "Left ventricular conditioning in the elderly patient to prevent congestive heart failure after transcatheter closure of the atrial septal defect," Catheter Cardiovasc. Interv., (2005), 64(3):333-337.
Stormer et al., "Comparative study of in vitro flow characteristics between a human aortic valve and a designed aortic and six corresponding types of prosthetic heart valves," European Surgical Research, (1976), 8(2):117-131.
Stumper et al., "Modified technique of stent fenestration of the atrial septum," Heart, (2003), 89:1227-1230.
Zhou et al., "Unidirectional valve patch for repair of cardiac septal defects with pulmonary hypertension," Annals of Thoracic Surgeons, (1995), 60:1245-1249.
Braunwald, Heart Disease, Chapter 6, p. 186 (no date available).
Bridges, et al., The Society of Thoracic Surgeons Practice Guideline Series: Transmyocardial Laser Revascularization, Ann Thorac Surg., 77:1494-1502 (2004).
Roven et al., "Effect of Compromising Right Ventricular Function in Left Ventricular Failure by Means of Interatrial and Other Shunts," American Journal Cardiology, 24:209-219 (1969).
Salehian et al., Improvements in Cardiac Form and Function After Transcatheter Closure of Secundum Atrial Septal Defects, Journal of the American College of Cardiology, 45(4):499-504 (2005).
Khositseth et al., Transcatheter Amplatzer Device Closure of Atrial Septal Defect and Patent Foramen Ovale in Patients With Presumed Paradoxical Embolism, Mayo Clinic Proc., 79:35-41 (2004).
Park Blade Septostomy Catheter Instructions for Use, Cook Medical, 28 pages, Oct. 2015.
Park, et al., Blade Atrial Septostomy: Collaborative Study, Circulation, 66(2):258-266 (1982).
Schmitto et al., Chronic heart failure induced by multiple sequential coronary microembolization in sheep, The International Journal of Artificial Organs, 31(4):348-353 (2008).
Trainor et al., Comparative Pathology of an Implantable Left Atrial Pressure Sensor, ASAIO Journal, Clinical Cardiovascular/Cardiopulmonary Bypass, 59(5):486-92 (2013).

\* cited by examiner

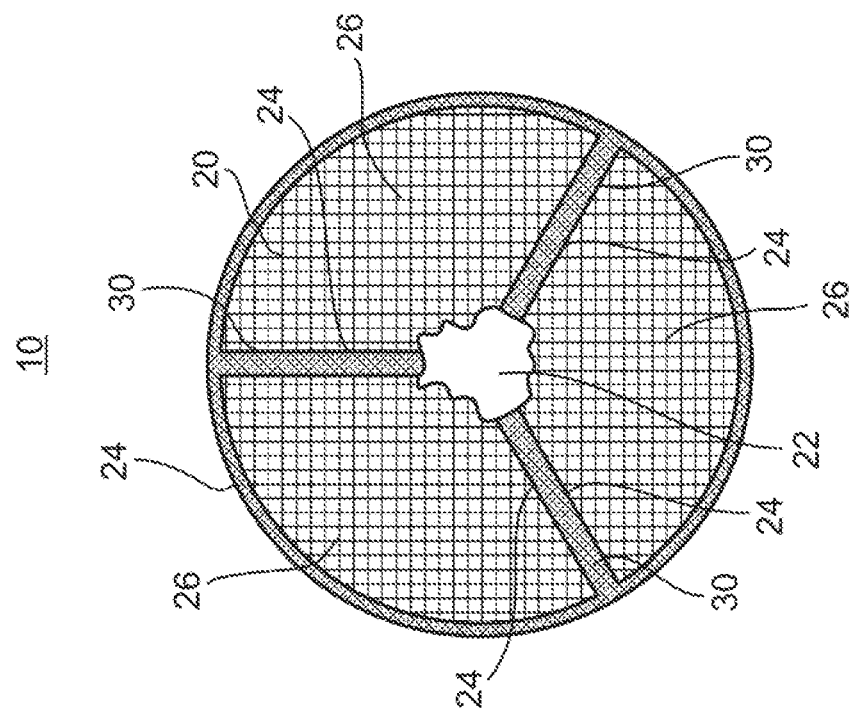
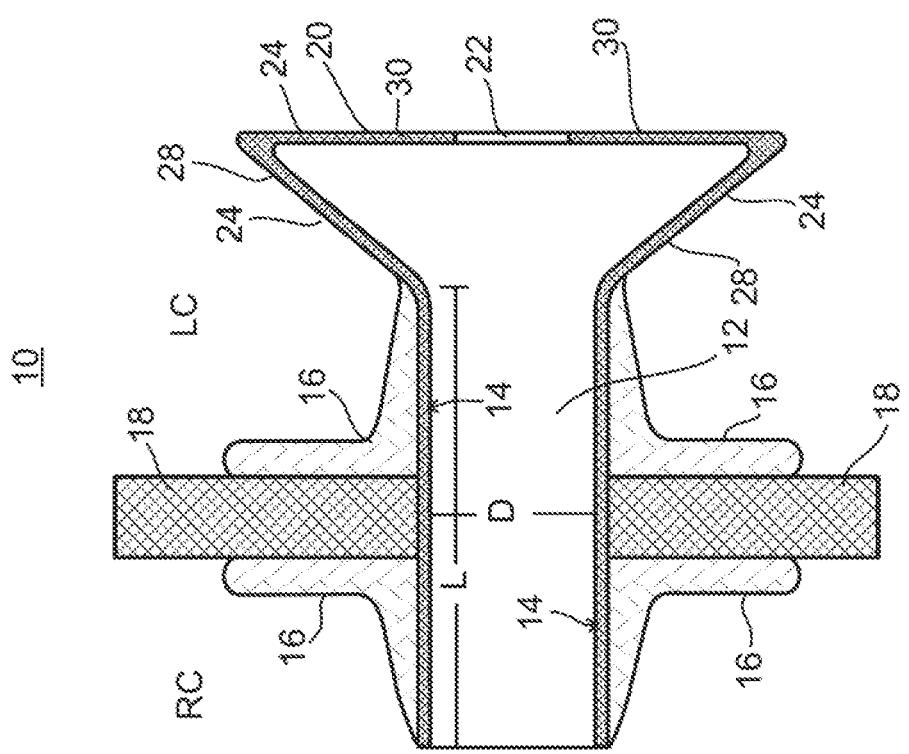
FIG. 1A
FIG. 1B

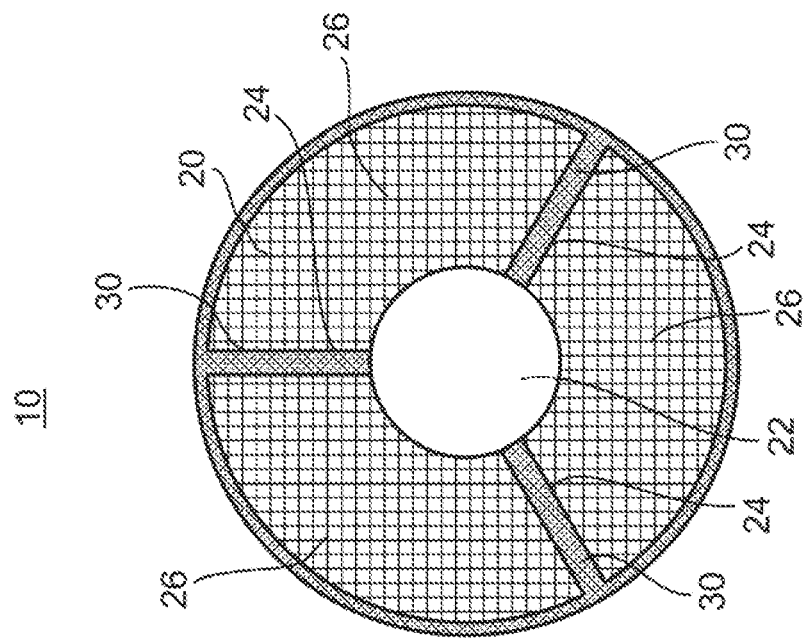
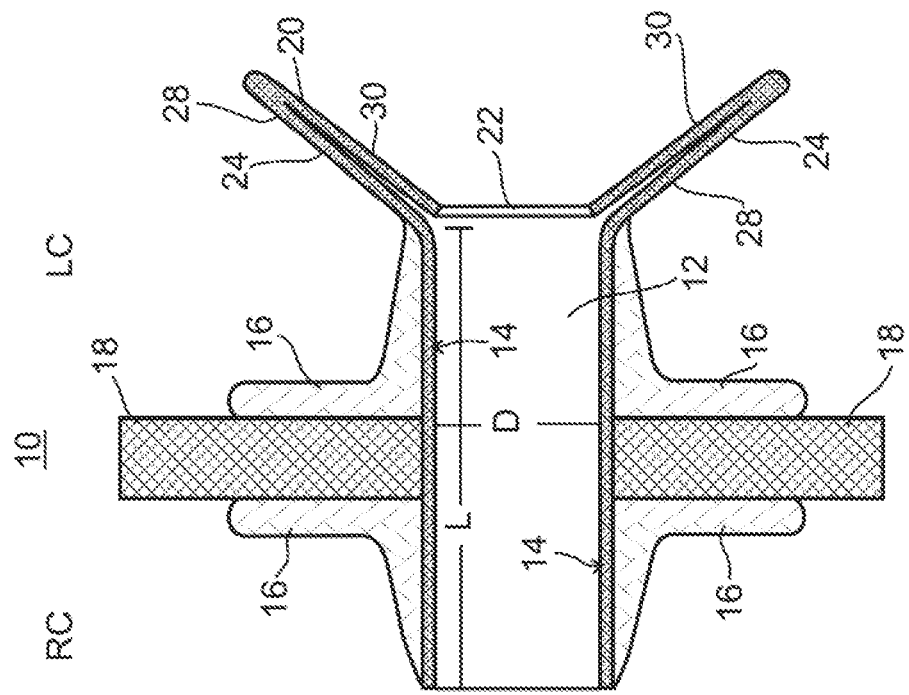

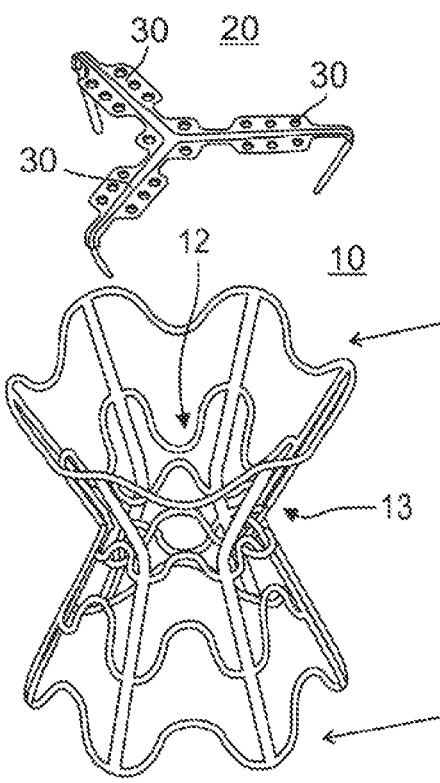
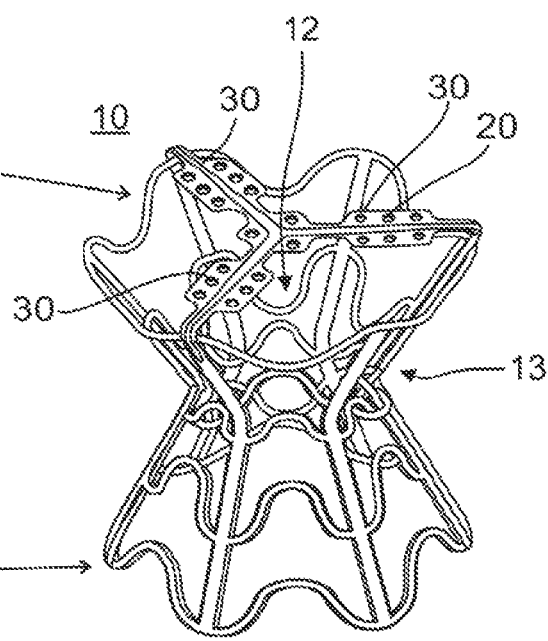
FIG. 5A          FIG. 5B
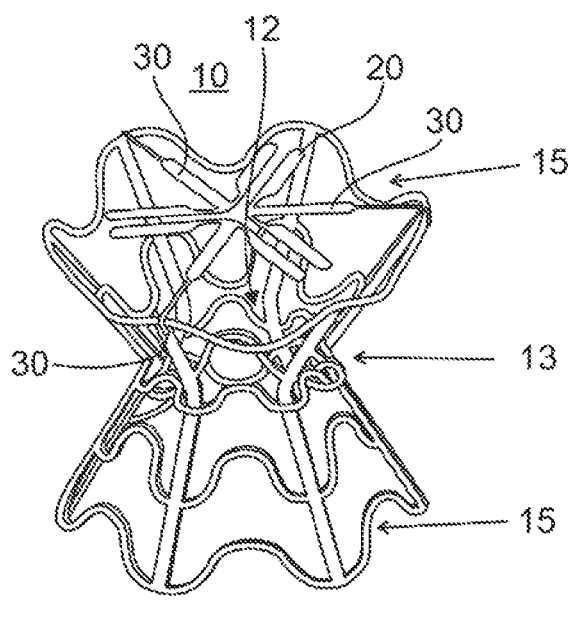
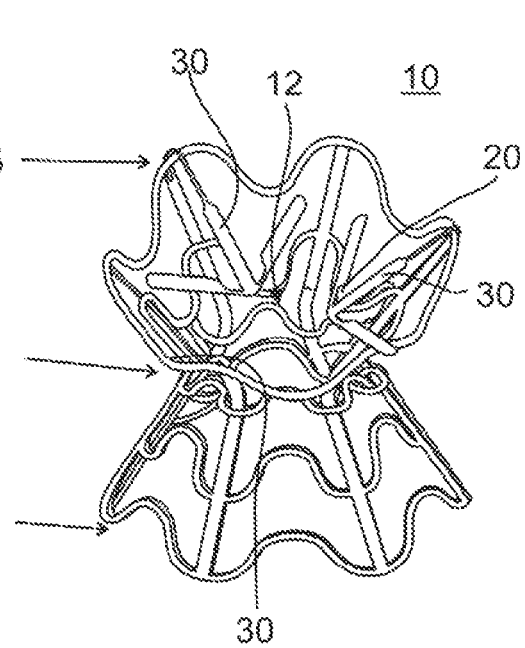
FIG. 5C          FIG. 5D

DEVICE AND METHOD FOR REGULATING PRESSURE IN A HEART CHAMBER

CROSS-REFERENCE TO RELATED APPLICATIONS

This application is a continuation under 35 U.S.C. §120 of U.S. patent application Ser. No. 13/108,880, filed May 16, 2011, now U.S. Pat. No. 8,696,611, which is a continuation under 35 U.S.C. §120 of International Patent Application No. PCT/IL2010/000354, filed May 4, 2010 and entitled "Device and Method for Regulating Pressure in a Heart Chamber," which claims the benefit of U.S. Provisional Patent Application No. 61/175,073, filed May 4, 2009, and U.S. Provisional Patent Application No. 61/240,667, filed Sep. 9, 2009, the entire contents of each of which are incorporated by reference herein.

FIELD

The present invention relates to a device which can be used to regulate pressure in a heart chamber. Specifically, the present invention relates to a device which can be used to lower a blood pressure in a left atrium in response to an increase in left atrial pressure and to a method of utilizing such a device in treatment of congestive heart failure related conditions such as Pulmonary Edema and decompensated heart failure caused by elevated pressures in a left side chamber of a heart.

BACKGROUND OF THE INVENTION

Congestive heart failure (CHF) is a condition in which the blood pumping function of the heart is inadequate to meet the needs of body tissue. CHF is one of the most common causes of hospitalization and mortality in Western society.

CHF results from a weakening or stiffening of the heart muscle most commonly caused by myocardial ischemia (due to, for example, myocardial infarction) or cardiomyopathy (e.g. myocarditis, amyloidosis). Such weakening or stiffening leads to reduced cardiac output, an increase in cardiac filling pressures, and fluid accumulation. Congestive heart failure (CHF) is generally classified as systolic heart failure (SHF) or diastolic heart failure (DHF).

In SHF, the pumping action of the heart is reduced or weakened. A common clinical measurement is the ejection fraction (EF) which is a function of the volume of blood ejected out of the left ventricle (stroke volume), divided by the maximum volume remaining in the left ventricle at the end of diastole or relaxation phase. A normal ejection fraction is greater than 50%. Systolic heart failure has a decreased ejection fraction of less than 50%. A patient with SHF may usually have a larger left ventricle because of phenomena called cardiac remodeling aimed to maintain adequate stroke-volume. This pathophysiological mechanism is associated with increased atrial pressure and left ventricular filling pressure.

In DHF, the heart can contract normally but is stiff, or less compliant, when it is relaxing and filling with blood. This impedes blood filling into the heart and produces backup into the lungs resulting in pulmonary venous hypertension and lung edema. Diastolic heart failure is more common in patients older than 75 years, especially in women with high blood pressure. In diastolic heart failure, the ejection fraction is normal.

CHF can be managed via a pharmacological approach which utilizes vasodilators for reducing the workload of the heart by reducing systemic vascular resistance and/or diuretics which prevent fluid accumulation and edema formation, and reduce cardiac filling pressure.

In more severe cases of CHF, assist devices, such as mechanical pumps can be used to reduce the load on the heart by performing all or part of the pumping function normally done by the heart. Temporary assist devices and intra-aortic balloons may be helpful. Cardiac transplantation and chronic left ventricular assist device (LVAD) implants may often be used as last resort. However, all the assist devices currently used are intended for improving pumping capacity of the heart and increasing cardiac output to levels compatible with normal life and are typically used to sustain the patient while a donor heart for transplantation becomes available. There are also a number of pacing devices used to treat CHF. Mechanical devices enable propulsion of significant amounts of blood (liters/min) but are limited by a need for a power supply, relatively large pumps and possibility of hemolysis and infection are all of concern.

Surgical approaches such as dynamic cardiomyoplasty or the Batista partial left ventriculectomy are used in severe cases, as is heart transplantation, although the latter is highly invasive and limited by the availability of donor hearts.

Although present treatment approaches can be used to manage CHF, there remains a need for a device for treating CHF which is devoid of the above described limitations of prior art devices.

SUMMARY OF THE INVENTION

According to one aspect of the present invention there is provided device for regulating blood pressure in a heart chamber comprising a shunt being positionable across the septum of the heart, specifically in the *fossa ovalis*, the shunt being for enabling blood flow between a left heart chamber and a right heart chamber, wherein a flow rate capacity of the device is a function of pressure difference between the left atrium and the right atrium.

In congestive heart failure the elevation in the left atrial pressure is higher than the elevation in the right atrial pressure and therefore the flow rate capacity is mainly regulated by the left atrial pressure changes.

In left heart failure, elevation of right heart pressure is also a function of left heart pressure. When the left atrium pressure rises neuro-hormonal compensatory mechanisms cause more endothelin secretion and less NO. This mechanism constricts the blood vessels and raises the right pulmonary artery pressure. If it wouldn't have occurred there would have been no flow across the pulmonary circulation. Therefore even though the flow across the present device is solely dependent on the pressure gradient between the left and right atrium it is correct to assume that its all a function of the left atrium pressure.

According to further features in preferred embodiments of the invention described below, the flow rate capacity of the device increases by 0.1-1.5 L/min when the average pressure in the left heart chamber is greater than 20 mmHg.

According to still further features in the described preferred embodiments the flow rate capacity of the device is 0.1-0.3 l/min when the average pressure in the left heart chamber is less than 20 mmHg.

According to still further features in the described preferred embodiments the device further comprises a valve for regulating flow through the shunt, wherein the valve increases a flow rate capacity of the device in response to an increase in pressure in the left heart chamber thus creating an increase in the differential pressure between the left and the right atria.

According to still further features in the described preferred embodiments the valve is a tissue valve.

According to still further features in the described preferred embodiments the tissue valve is a pericardium tissue valve.

According to still further features in the described preferred embodiments the pericardium tissue is derived from a Porcine, Equine, or Bovine source.

According to still further features in the described preferred embodiments a fluid conduit of the shunt increases in cross section area with the increase in pressure in the left heart chamber According to still further features in the described preferred embodiments the device further comprises anchoring elements for attaching the device to the septum.

According to still further features in the described preferred embodiments the device further comprises anchoring elements for attaching the device to the septum.

According to still further features in the described preferred embodiments the device is diabolo-shaped such that the device only contacts tissue forming the opening in the septum and not tissue surrounding the opening.

According to still further features in the described preferred embodiments the diabolo shape does not allow migration of the valve through the septum.

According to another aspect of the present invention there is provided a method of assessing the hemodynamic condition of a subject comprising implanting the present device in the subject and determining flow through, or valve leaflet angle of, the device, the flow through or leaflet angle being indicative of left atrial pressure.

According to still further features in the described preferred embodiments, determining is effected via an imaging approach such as ultrasound, fluoroscopy, MRI and the like.

The present invention successfully addresses the shortcomings of the presently known configurations by providing a device which can more accurately compensate for a disordered hemodynamic state of a heart of a CHF patient and which can be implanted using minimally invasive approaches.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A-B illustrate a side view (FIG. 1A) and a frontal view (FIG. 1B) of a device for regulating pressure in a heart chamber constructed according to one embodiment the present invention and showing the valve component in the closed position.

FIGS. 2A-B illustrate a side view (FIG. 2A) and a frontal view (FIG. 2B) of the device of FIGS. 1A-B showing the valve component in the open position.

FIG. 5A-D illustrate isometric views of a diabolo shaped device of the present invention. FIG. 5A separately illustrates the device body and valve substructures, while FIGS. 5B-5D illustrate the assembled device. The valve is shown in a closed position in FIGS. 5B-5C, and in an open position in FIG. 5D.

DETAILED DESCRIPTION

Figure 3:
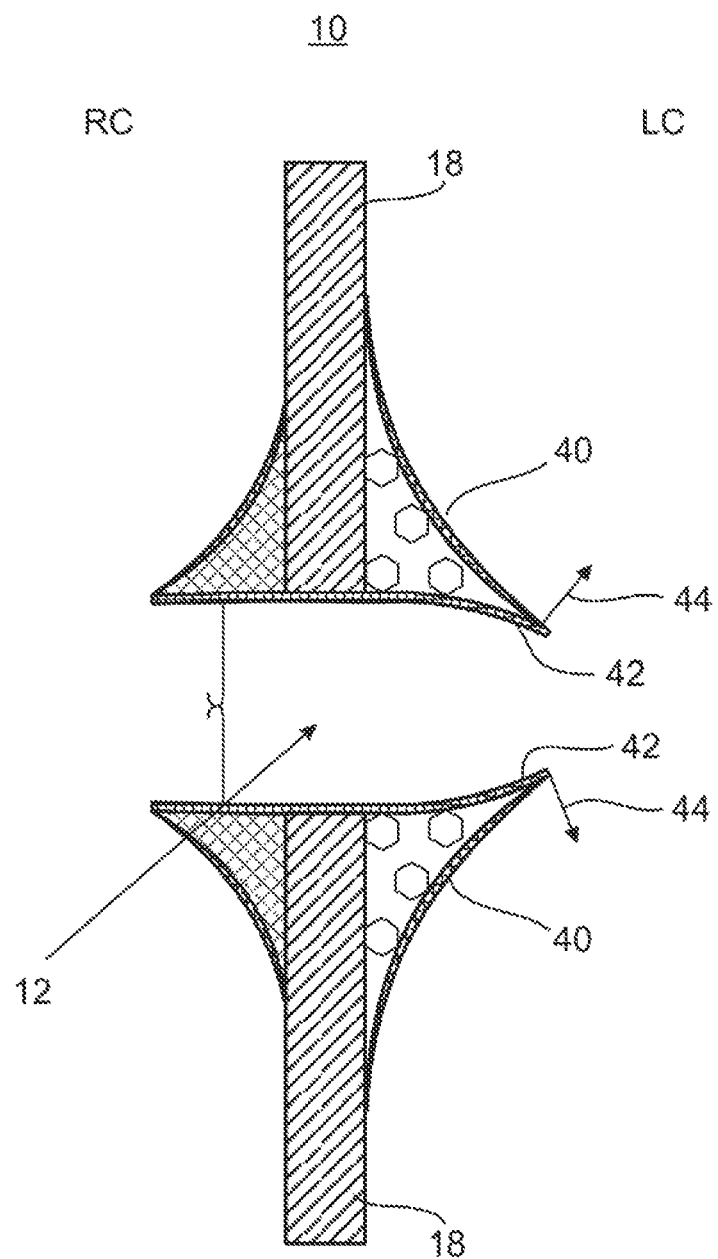
FIG. 3 illustrates a side view of a device for regulating pressure in a heart chamber constructed according to another embodiment the present invention.

The present invention is of a device and method which can be used to regulate pressure in a heart chamber. Specifically, the present invention can be used to treat elevated chamber pressures present in a patient suffering from CHF or having a Patent Foramen Ovale (PFO) or an Atrial Septal Defect (ASD) that requires repair and prevention of embolization from right to left atriums but is preferably left with residual flow between atriums so as not to traumatize heart hemodynamics.

The present device can also be used to determine the pressure in the left atrium and thus assist in defining the exact clinical condition of the patient which can be used to alter/adjust patient medication and help stabilize hemodynamics.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

CHF is one of the most common causes of hospitalization and mortality in Western society. At present, CHF is treated using pharmaceutical, mechanical or surgical approaches.

In an attempt to traverse the limitations of prior art approaches, Applicant has devised a novel minimally invasive approach for reducing the disordered hemodynamics associated with CHF. Such an approach, which is described in US 20020173742 and 20070282157, the entire contents of each of which are incorporated herein by reference, utilizes a device which includes a shunt which is positioned between heart atria and enables blood flow between the left and right atria. The device includes an adjustable flow regulation mechanism which is configured for regulating the flow of blood through the shunt in relation to a pressure differential between the chambers.

While reducing the present invention to practice, the present inventors have continued to experiment and model this approach and have surprisingly discovered that disorders or conditions which result from abnormal heart hemodynamics, such as those characterizing CHF, can be treated by regulating blood flow between heart chambers mostly as a function of left chamber pressure.

Thus according to one aspect of the present invention there is provided a device for regulating blood pressure in a heart chamber, such as a ventricle or an atria.

As is further described hereinbelow, the present device can be used in human subjects suffering from CHF as well as in subjects which have septal defects but are not candidates for complete septal closure.

The device includes a shunt which preferably includes a valve for controlling flow through the shunt. The device is positionable within a septum of the heart and is configured for enabling blood flow between a left heart chamber and a right heart chamber. The device is configured such that a flow rate capacity thereof is a function of (blood) pressure gradient between the left and right atria. Because the right atria pressure is mostly affected from the left atria pressure, flow regulation is mainly governed by the left atria pressure.

In a normal heart, beating at around 70 bpm, the stroke volume needed to maintain normal CO (Cardiac output) is between 60 ml-100 ml. When the preload, after-load and contractility are normal, the pressures needed to achieve this CO values are as described in Table 1 below. In CHF the Hemodynamic parameters change (Table 1) because in order to maximize CO the heart needs higher pressures to either overcome the higher after-load or lower contractility or damaged preload.

TABLE 1

Ranges of heart parameters in normal and CHF heart

| Parameter | Normal Range | CHF Range |
|---|---|---|
| Right Atrial Pressure (RAP) | 2-6 mmHg | 6-15 mmHg |
| Right Ventricular Pressure (RVP) | 15-25 mmHg | 20-40 mmHg |
| Left Atrial Pressure (LAP) | 6-12 mmHg | 15-30 mmHg |
| Left Ventricular Pressure | 6-120 mmHg | 20-220 mmHg |
| Cardiac Output (CO) | 4.0-8.0 l/min | 2-6 l/min |
| Stroke Volume (SV) | 60-100 ml/beat | 30-80 ml/beat |

Thus, reduction of left chamber blood pressure, and in particular left atrial pressure (LAP), can be used to offset abnormal hemodynamics characterizing CHF and other heart pathologies and thereby treat conditions associated therewith. For example, the present invention can be used to treat pulmonary edema associated with CHF. Pulmonary edema, which is the most severe manifestation of CHF, develops when an imbalance in the heart pumping function causes an increase in lung fluid secondary to leakage from pulmonary capillaries into the interstitium and alveoli of the lung.

As is described in detail in Example 1 of the Examples section which follows, the present device can be used to alleviate such an imbalance by regulating flow from the left atrium to the right atrium (through a septum). The flow capacity of the present device changes mainly due to changes in left atrial pressure and as a result, flow from the left atrium to the right atrium is mainly a function of the left atrial pressure.

The insight gained by the present inventors from experimenting with various device configurations and modeling blood flow between heart chambers, has led to the formulation of several design parameters:

(i) Changes in left chamber pressure directly affect flow capacity (thus volume) through the device thereby resulting in LA decompression and prevention of pulmonary congestion.

(ii) In situation where peak left chamber pressure exceeds a predetermined amount, pressure is lowered by increased flow capacity in the device, for example, in cases where LAP exceeds 25 mmHg, increased flow capacity decreases LAP by 3-6 mmHg.

(iii) The flow capacity of the present device gradually changes starting at left atrial pressure (LAP) of about 15 mmHg and reaches full capacity at an LAP of 25 mmHg. The device can be designed with characteristics that are patient dependent i.e. if a patient is screened and found to be at pulmonary Edema risk at 20 mmHg then the device is configured for reaching full flow capacity at 20 mmHg.

(iv) The flow capacity of the present device starts to change when the pressure gradient across the septum is between 5 mmHg-10 mmHg. Up to 5 mmhg the valve of the present device remains substantially closed. Between 5-10 mmHg the valve slightly opens and flow of up to 0.5 l/min is supported. At gradients between 10-20 mmHg the flow across the valve rapidly increases as a function of the opening of the leaflets. The flow reaches 1.5 l/min at 20 mmHg. Above 20 mmHg the valve is fully open and the flow is defined by the narrow part of the lumen of the device (in the diabolo configuration, the narrow portion can be between 4-6 mm depending on the configuration).

(v) The device is patient specific i.e. in patients where the pressure gradients are very high the valve will be built such that the min opening gradient will be higher than in those patients where the gradients are lower. For example: if the patient has a mean LA gradient of 16 mmHg and mean RA pressure of 8 mmhg the valve will be assembled with the parameters described in (iv). If however, the mean LA pressure is 23 mmHg and the mean RA pressure is 8 mmHg the minimal valve opening will be at 10 mmhg and full opening will only occur at the 25 mmHg gradient.

(vi) The device is designed to allow constant flow regardless of left chamber pressure to maintain its patency over time. Constant flow refers to a flow during each heart cycle. However in each cycle, if the mean left atrial pressure is below 20 mmHg, flow will only occur during the V-Wave of the atria. The V-Wave of the atria occurs at the end of the atria's diastole. CHF patients, especially those having mitral regurgitation, have V-Waves characterized by very high pressure that can reach up to 40 mmHg for up to 150 ms of each heart beat. The rest of the cycle the left atrium pressure drops. In such patients, the present device will enable flow that maintains the patency of the device only for a short duration (less than 15%) of each cycle, and thus the flow across the valve of the present device will be less than 0.3 L/min and there will be negligible effect on the cardiac output.

(vii) A diameter of a shunt (conduit) of the device changes from 0-6 mm as a function of the pressure changes to prevent large volume flow when left chamber pressure is below a predetermined threshold (e.g. when LAP is below 25 mmHg).

(viii) The device is configured to prevent right chamber blood from entering the left chamber under elevated right chamber pressure conditions where RAP is higher than LAP. Selecting a shunt length of above 10 mm prevents RA blood from reaching the Left Atrium also during onset of slightly higher RA-LA pressure gradient. Another feature that disables right to left shunting is the valve that is normally closed when pressures in the right atrium are slightly higher than in the left atrium. In CHF caused by left heart failure there are almost no cases where there is a higher right atrium pressure. Therefore prevention of flow in pressures gradients of less than 5 mmHg eliminates the risk of right to left shunting in CHF patients.

(ix) When left chamber pressure is below a predetermined threshold (e.g. below 25 mmHg in the LA), the device is designed to minimize CO reduction to less than 0.1 l/min.

(x) A reduced flow capacity under pressures that are below a predetermined threshold ensures that the device prevents RV overload, and maintains Qp/Qs<1.3.

(xi) The Device can also be designed to allow controlled tissue growth (up to 1 mm thickness) to become inert over time but not to lead to occlusion by excessive growth in or around the shunt.

To enable such functionality, the present device is an intra-septal implant which is attached to a septum separating two heart chambers (e.g. left atria from right atria or left ventricle from right ventricle). The device includes a shunt and optionally a valve having an opening capable of changing its diameter mainly as a function of the left chamber pressure.

The present device is preferably designed having a 5 mm opening diameter following implantation and tissue ingrowths. The device is configured for maintaining constant flow through the V-wave portion of each heart cycle at about 0.1-0.3 l/min. The maximum opening diameter of the shunt/valve is preferably 5 mm to enable an approximate maximum flow capacity of 1.5 l/min.

The device of the present invention or a portion thereof (e.g. valve) is preferably constructed from a laser cut tube to a shape of a stent, covered by ePTFE to create a shunt and a tissue valve at the left atria's end (Pericardium equine, Bovine, Porcine between 0.1 mm-0.5 mm tissue thickness) which is sutured or welded to the frame. To enable percutaneous delivery, the present device can preferably be collapsed to an overall diameter of less than 15 F.

Embodiments of the device of the present invention suitable for use in regulating left atrial pressure are illustrated in FIGS. 1a-3. It will be appreciated that although the following describes use of the present device in regulating LAP, alternative uses in regulating LVP, RAP or RVP are also envisaged by the present inventors.

FIGS. 1A-1B illustrate one embodiment of the present device which is referred to herein as device 10. FIGS. 1A-1B illustrate a cross sectional view (FIG. 1A) or a frontal view (FIG. 1B) of device 10 in a configuration in which flow capacity is at a minimum.

Device 10 includes a shunt 12 which serves as a conduit for blood flow between a left chamber (LC) and a right chamber (RC). Shunt 12 is configured as a tube having a diameter (D) selected from a range of 3-10 mm. Shunt 12 can be constructed from a polymer such as silicone, ePTFE, or Dacron via extrusion or molding or from an alloy (e.g. titanium, NITINOL, Cobalt Chromium and the like). It can also be constructed from tissue derived from vein grafts or pericardium. In any case, shunt 12 preferably includes a tissue outer structure and potentially an inner polymer cover. The tubular frame of shunt 12 can be constructed by cutting a tube or by wrapping a wire over a mandrel and covering the resultant tubular structure with animal tissue (e.g. pericardium derived from bovine, equine or porcine tissue), PTFE or Dacron which is sutured or welded to the frame. Since walls 14 contact blood as it flows through shunt 12, such walls can be coated or impregnated with carbon, heparin and endothelial cells. Such coating can be used to reduce drag and prevent blood coagulation and formation of clots and to promote controlled tissue growth. Alternatively, walls 14 can be textured or provided with fine electropolished smooth metal surfaces in order to increase laminar flow and decrease turbulence.

Shunt 12 is selected having a length (L) of 10-20 mm and a wall 14 thickness of 0.1-0.5 mm.

Device 10 further includes anchoring elements 16 which serve to anchor shunt 12 to septum 18. Anchoring elements are designed for anchoring septal tissue. The device will be implanted in the septum preferably in the Fossa Ovalis were the wall thickness is between 0.2-1 mm. In that respect, septal anchoring is preferably effected by expanding the diameter of shunt 12 at least 2 mm larger than the Transeptal puncture diameter used for implantation. This expansion will give the radial stiffness needed to hold the implant in place. Furthermore anchoring elements 16 are configured for applying axial pressure against the septum to thereby add friction that will prevent relative movement between device 10 and the septum. Such pressure is achieved by the shape of device 10 when in position. Anchoring elements 16 can be constructed from a NITINOL wire mesh or a Polymer (e.g. Dacron, ePTFE) sutured to the wire. Anchoring elements 16 are configured with an elastic force directed towards each other such that when device 10 is positioned, anchoring elements 16 apply opposing inward forces to the septal tissue.

Since implantation of device 10 within the septum will lead to tissue growth around device 10 in response to injury, anchoring elements 16 and shunt 12 are designed to compensate for such tissue growth. For example, device 10 or any of its components can be seeded with endothelial cells or coated with heparin or impregnated with carbon in order to controlled tissue growth and prevent clot formation.

Shunt 12 is designed such that tissue ingrowth will not be excessive. Ends of shunt 12 protrude from the septal plane to minimize rapid tissue growth. Device 10 is also designed to minimize an effect on atrial flow in order not to cause hemolysis. In that respect, ends of shunt 12 do not protrude by more than 7 mm into opposing Atria and in addition the surfaces of shunt 12 exposed to flow are preferably rounded.

In the embodiment shown in FIGS. 1A-2B, device 10 also includes a valve 20 which functions in regulating flow through shunt 12. In this embodiment, the flow capacity of shunt 12 is fixed, however, flow therethrough is regulated by a diameter of opening 22 of valve 20 and as such the overall flow capacity of device 10 falls within a preset range (e.g. 0.2-1.5 l/min).

Valve 20 can be constructed having any configuration capable of supporting baseline (minimal) flow when in a closed position (Shown in FIGS. 1A-1B) while being capable of a gradual or binary response to left chamber pressure which exceeds a predetermined threshold (e.g. above 25 mmHg in left atrium). Valve 20 includes a frame 24 which is constructed from a polymer or an alloy (e.g. NITINOL) with overstretched polymer or tissue (as described above for shunt 12). Valve 20 can be attached to shunt 12 or constructed as an extension thereof (contiguous).

Construction of device 10 of FIGS. 1A-2B is described in detail in Example 2 of the Examples section which follows.

Opening 22 in valve 20 is formed in front wall 26 of valve 20. In the case of valve 20 constructed from frame 24 and covering of a polymeric material or tissue, opening 22 can be constructed by overlapping leaflets of polymer or tissue. The valve can be cut from one or three leaflets that are sutured or welded to their commisures in the closed position of the valve thus leaving a slack that once stretched leads to enlargement of opening 22.

A binary response configuration of valve 20 assumes one of two states, a closed state (FIGS. 1a-b) which supports flow of 0.1-0.5 l/min or an open state (FIGS. 2A-2B) which supports flow of 0.5-1.2 l/min. Such a binary configuration can be constructed by, for example, designing frame 24 to be capable of assuming one of two states in response to pressure applied to front (26) or side (28) walls of valve 20. The frame of valve 20 includes NITINOL commisures that under predetermined forces (few grams) are able to rotate inwards. This is achieved by a designing such commisures with a preset bending response.

A gradual response configuration of valve 20 includes a frame 24 or walls 26 or 28 that are configured capable of changing conformation in response to pressure elevation in a gradual or stepwise manner. In such cases, diameter of opening 22 of valve 20 can increase from 1-3 mm (closed state) in increments of, for example, 1 mm in response to changes in pressure of 5 mmHg.

In the configuration shown in FIGS. 1A-2B, valve 20 is capable of a gradual opening response to increases left chamber pressure. Such gradual response is enabled by use of arms 30 forming a part of frame 24. As is shown in FIGS. 2A-2B, pressure applied to front walls 26 of valve 20 rotates arms 30 inward (towards shunt 12) thereby increasing diameter of opening 22. In such a configuration, a rise in pressure of 5-10 mmHg (over a threshold, e.g. 25 mmHg in the LA), translates to an increase of 5-10 grams of force in walls 26 and rotation of arms 30 45 degrees inward. In a preferred configuration of device 10, rotation of arms 30 45 degrees inward results in an increase diameter in opening 22 from 3 to 5 mm.

FIG. 3 illustrates another embodiment of device 10. In this embodiment flow through shunt 12 is controlled by a sail-like element 40 which is disposed completely in the left Atrium. When the pressure in the LA rises above a predetermined threshold elements 42 are pushed towards the Septum. This movement pulls valve flaps 42 outward (in the direction of arrows 44) thereby increasing flow through shunt 12.

Although the above described embodiments of device 10 are presently preferred, additional embodiments of device 10 which can provide the functionality described herein are also envisaged. Any configuration which can be used to increase flow in shunt 12 as a function of Left chamber pressure increase can be used with the present invention. This includes a shunt 12 designed with a collapsible conduit (e.g. fabricated from soft, pliable silicone), which is forced open by pressure changes.

Device 10 of the present invention can be configured to support any flow capacity of therapeutic value and be capable of any response profile to increasing or decreasing chamber pressures. Preferably, device 10 supports a minimal flow capacity of 0.1-0.3 and a maximal flow capacity of 0.6-1.2 l/min under increased left chamber pressure. In cases of atrial implantation and conditions characterizing SHF, device 10 supports a flow capacity of 0.1-0.5 l/min at LAP of less than or equal to 25 mmHg and a flow capacity of 0.6-1.2 l/min at LAP greater than 25 mmHg. In cases of atrial implantation and conditions characterizing DHF, device 10 supports a flow capacity of 0.1-0.3 l/min at LAP of less than or equal to 25 mmHg and a flow capacity of 0.5-1.2 l/min at LAP greater than 25 mmHg. Such a pressure versus shunt diameter curve is not linear but is preferably exponential.

FIGS. 4A-4D illustrate yet another embodiments of device 10 of the present invention. The configuration exemplified by this embodiment is responsive (in as far as changes to flow capacity) to either LA-RA pressure differential or to left atrial pressure only as is the case with the configurations described above. In this configuration, valve 20 can fully close under low a pressure differential lower than a predetermined threshold or under LA pressure lower than a threshold. Such complete closure prevents any flow from the LA to the RA.

Figure 4A:
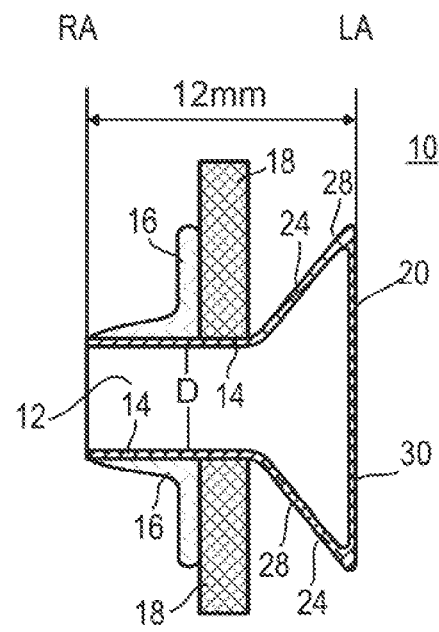
FIGS. 4A-D illustrate side (FIGS. 4A, 4C) and frontal (FIGS. 4B, 4D) views of another embodiment of the present device in closed (FIGS. 4A-4B) and open (FIGS. 4C-4D) positions.
Figure 4B:
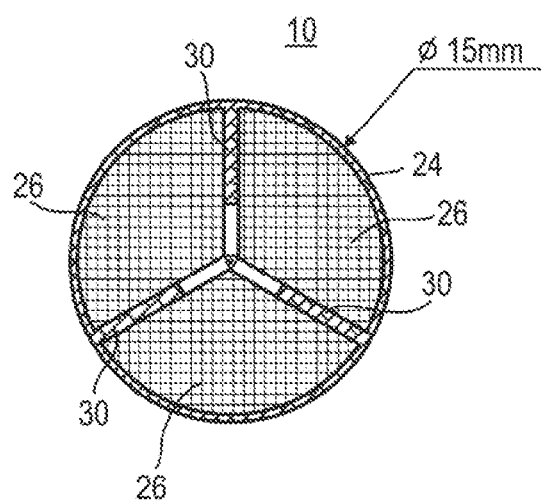
Figure 4C:
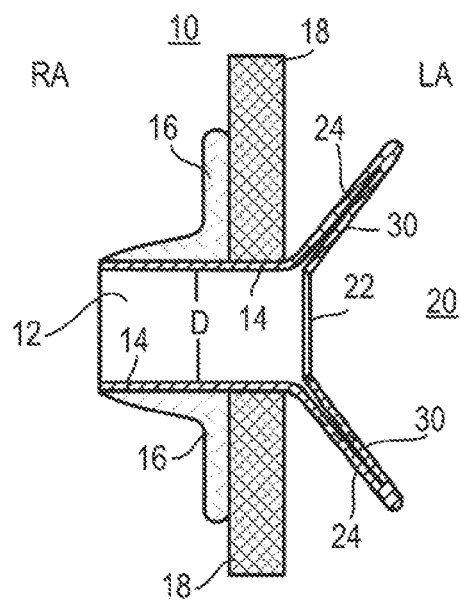
Figure 4D:
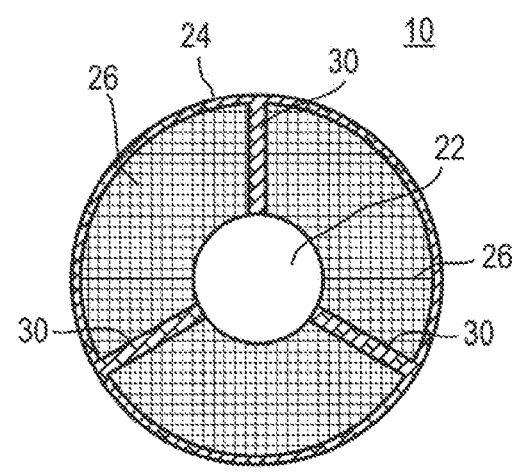

Components of device 10 are as described above. Valve 20 includes front walls 26 (leaflets) that are sutured to arms 30 (commisures). Arms 30 can be constructed from NITINOL which at a pressure differential higher than 8 mmHg (i.e. the pressure difference between the right and left sides of walls 26 as shown in FIG. 4a) will elastically deform in the direction of the RA to thereby open valve 20 and enable blood flow from the LA to the RA. Such opening of valve 20 can be gradual up to a maximum achieved at a pressure differential of 10 mmHg. Likewise when the pressure differential decreases to below 5 mmHg, valve 20 will close completely.

Valve 20 of this embodiment of device 10 opens and closes with each heart cycle as a response to an RA-LA pressure differential.

Such a pressure differential fluctuates between diastolic and systolic phases of each heart cycle. In chronic CHF patients, peak LA pressure is below 25 mmHg and thus the LA-RA pressure differential is around 5 mmHg in the diastolic phase and 10 mmHg in the systolic phase. Valve 20 is designed to start opening (increasing flow capacity through shunt 12) at a pressure differential higher than 5 mmHg. As a result, in chronic CHF, shunt 12 will support maximal flow capacity at the systolic phase of each heart cycle and minimal flow capacity at the diastolic phase. This will result in a net flow (LA to RA) of less than 0.3 l/min.

During acute stages when the LA pressure is higher than 25 mmHg, valve 20 will be fully open, this will result in a net flow (LA to RA) of 1.5 l/min thereby decreasing the LA pressure by 5 mmHg.

FIGS. 5A-5D illustrate yet another configuration of device 10 of the present invention. In this configuration, shunt 12 is housed in a diabolo-shaped body which is constructed from an alloy such as stainless steel or NITINOL using methods well known in the art of stent making. A diabolo-shaped body is advantageous for septal anchoring and the prescribed function of device 10. A diabolo shape ensures that a device 10 positioned within a septum opening is trapped therein due to the fact that the region of minimal diameter of device 10 (indicated by 13 in FIGS. 5A-5D) traverses the septal opening while the larger diameter ends flank the opening and do not contact the tissue. This anchoring configuration also minimizes irritation to septal tissue since contact between device 10 and the tissue is minimized. Since the larger diameter ends (15 in FIGS. 5A-5D) of device 10 flank the septal opening and cannot move through the opening therein, device 10 is essentially trapped and secured within the opening. In addition, such trapping (passive anchoring) ensures that device 10 remains in position during septal wall movement, dilation of the septal opening and flow of blood through shunt 12 while accommodating such movement without applying forces to the septal tissue which might result in tissue damage.

The configuration of device 10 depicted in FIGS. 5A-5D also includes a valve 20 which is constructed from elastic arms 30 which can be separately connected to the body of device 10 (FIGS. 5C-5D) by way of welding, suturing, or interconnected at ends thereof into a single structure as shown in FIGS. 5A-5B). Arms 30 can be covered with tissue or PTFE membranes (not shown) in a manner similar to that described above. Arms 30 can move between a closed position (as shown in FIGS. 5B-5C) which minimizes or blocks flow and one or more open positions (FIG. 5D) which support flow at predetermined flow rates according to a pressure or a pressure differential at valve 20 (The force of bending each arm until it reaches the stent is 5 grams). In this respect, valve 20 of this device 10 configuration functions in a manner similar to valve 20 described above with reference to alternative device 10 configurations.

Device 10 is delivered via a standard trans-septal puncture procedure. A trans-septal puncture is made as described below and a 12-16 F sheath is inserted into the septal opening from the RA venous system from the inferior vena Cava side. Device 10 is fed into the distal end of the sheath (protruding into the LA) via a tapered loader and pushed into the sheath to the point where the LA side of device 10 protrudes from the distal side of the sheath. The LA side of device 10 is then expanded (by pushing the valve into the LA). The sheath, with the device, is then pulled into the RA to the point where the expanded LA side of device 10 contacts the septum. In this position the sheath is pulled back (in the direction of the RA) exposing the RA side of device 10 and locking it within the septum. The Loader and sheath are then removed.

In the expanded configuration, device 10 is about 13 mm in length, with a minimal diameter of 4-8 mm (at 13) and a maximal diameter of 10-16 mm (at 15). In the compressed (deliverable) configuration, device 10 is 10-18 mm in length and 3-6 mm in diameter.

As is mentioned hereinabove, different patients may exhibit slightly different hemodynamic parameters (e.g. different left atrial pressure). Thus, to meet the needs of different patients, device 10 can be configured as part of a kit which includes several variants of device 10, each having slightly different characteristics (such as device 10 length, diameter of shunt 12, pressure threshold for increasing opening 22 of valve 20 and the like). Such a kit enables a physician to match a patient with the most suitable variant of device prior to implantation.

Alternatively, device 10 can be configured modifiable post implantation. Such a configuration of device 10 can include elements which can be adjusted post implantation to thereby modify device 10 characteristics to match the hemodynamic profile of the patient.

One example of such a configuration can include a device 10 which can have a shunt 12 conduit which can be expanded to a predetermined diameter suing a balloon catheter.

Preferred flow parameters of device 10 of the present invention are described in detail in Example 1 of the Examples section which follows.

As is mentioned hereinabove, device 10 of the present invention can be utilized in treatment of CHF as well as other disorders. In the case of CHF, device 10 is preferably positioned in a septum between atria using a minimally invasive delivery system.

Thus, according to another aspect of the present invention there is provided a system for regulating pressure in a heart chamber.

The system includes a delivery catheter capable of delivering device 10 to a heart septum and a sheath, a push-rod, a transeptal puncture device and haemostatic valves Implantation of device 10 is effected via transfemoral approach. A catheter is delivered through a sheath placed through the femoral vein and up into the Vena Cava into the RA. A transeptal puncture device is deployed from the delivery catheter and the middle of the Fossa Ovalis of the septum is controllably punctured and then dilated via a balloon catheter to 7 mm (switched through the sheath). A pressure transducer catheter is then used to collect hemodynamic parameters from the left and right atria over at least one complete heart cycle to thereby derive patient-specific parameters such as left atrial pressure during diastole and systole and the like. These parameters will enable selection of a device 10 having characteristics (e.g. flow capacity of shunt in the closed and fully open positions, length of device 10) which best match the needs of the patient.

The device 10 selected is then loaded onto a delivery catheter and delivered to the septum. Device 10 is pushed out of the access sheath and into the LA using the push-rod deployed from the delivery catheter, such positioning deploys the anchoring elements on the RA side. The catheter is then retracted to position the device in place in the LA and deploy the anchoring elements at the LA side.

Such transplantation of device 10 of the present invention through a septum of a subject can be used to treat CHF-related conditions as well as be used in cases of septal or atrial defects which cannot be effectively treated via standard approaches.

The present device can also be used to determine the pressure in the left atrium and thus assist in assessing the clinical condition of the patient. Such an assessment can be used to adjust the medication given to the patient and help stabilize the patient's hemodynamic condition.

Left atrial pressures can be determined by visualizing, using imaging modality such as echo ultrasound, an angle of the leaflets of the valve of the present device or by quantifying the flow across the valve. The angles of the leaflets or the flow across the valve will correlate to a specific pressure gradient between the left and right atrium thus correlate to the pressure in the left atrium. By quantifying the pressure in the left atrium the physician can adjust the medications given to the patient and help in stabilizing the hemodynamic condition of the patient and prevent edema. Example 4 of the Examples section which follows provides further detail with respect to leaflet angle and flow measurements calculations.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Flow Calculations

The present inventors have calculated the flow needed to reduce left atrial pressure (LAP) to below 25 mmHg. For the purpose of calculations it was assumed that under SHF and DHF, the LAP minimum and maximum pressures are the same (12 mmHg & 28 mmHg respectively). In order to treat these conditions, LAP must be reduced by 3-5 mmHg.

The following parameters were taken into consideration:
(i) SHF cardiac output (CO)=2.5-4 l/min heart rate (HR)= 75 (ii) DHF CO=3-5.5 l/min HR=70. In SHF one can assume a linear correlation between LA pressure and volume (Pstatic fluid=ρgh), and thus one can calculate the following:

In SHF: LAP—16 mmHg, Filling volume—50 cc each cycle. Reducing LAP by 3-5 mmHg i.e. 3-5/16=20%-30% requires 20%-30% less blood i.e. 10 cc-16 cc of blood each heart beat which translates to ~0.75 l/min to 1.2 L/min LA-RA flow in SHF [10 cc & 16 cc×75(HR)]

To find an optimal shunt diameter, one can use Bernouli's equation and assume no viscosity due to the short length of the shunt (few mm at narrowest diameter):

$$Q = CeE \frac{\pi D_2^2}{4} \sqrt{\frac{2(p_1 - p_2)}{\rho}}$$

Where Q (Flow)=1.2 l/min, C(Discharge Coefficient)=0.7, e (expansion)=NA (for gasses only), P1-P2 (LAP-RAP after shunting)=6 mmHg, and ρ=1.05 gr/cm³.

A shunt diameter of 4 mm supports a flow capacity of 0.75 l/min, and a 3 mmHg reduction in LAP, a shunt diameter of 5.5 mm supports a flow capacity of 1.3 l/min & and a 5 mmHg reduction in LAP.

Once the shunt is positioned, the first few heart cycles will enable 1 l/min flow until the pressure is below 25 mmHg. When the shunt supports 1 l/min one can expect ~0.3 l/min CO reduction. This is because of the compensatory mechanisms in CHF.

Figure 7:
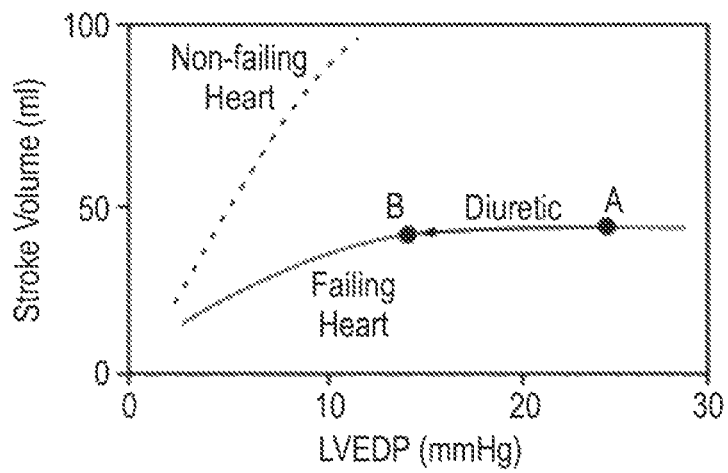
FIG. 7 is a curve illustrating a stroke volume—left ventricle end diastolic (LVED) pressure relationship in a failing and non-failing heart.
Figure 8:
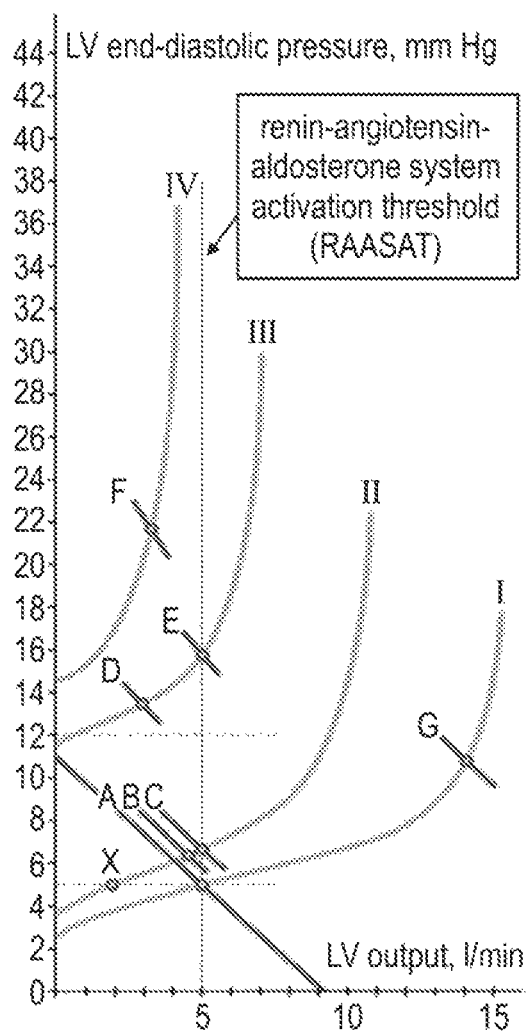
FIG. 8 is a curve illustrating a left ventricle end diastolic (LVED) pressure—left ventricle (LV) output relationship in patients classified according to the severity of the condition. Class I (Mild)—no limitation of physical activity. Ordinary physical activity does not cause undue fatigue, palpitation, or dyspnea (shortness of breath). Class II (Mild)—slight limitation of physical activity. Comfortable at rest, but ordinary physical activity results in fatigue, palpitation, or dyspnea. Class III (Moderate)—marked limitation of physical activity. Comfortable at rest, but less than ordinary activity causes fatigue, palpitation, or dyspnea. Class IV (Severe)—unable to carry out any physical activity without discomfort. Symptoms of cardiac insufficiency at rest. If any physical activity is undertaken, discomfort is increased.

Both in SHF and DHF the heart is working on the plateau of the Starling curve. The additional pressure is not correlated to additional stroke volume (FIG. 7). The additional volume is translated to high pressures and edema. Therefore by slightly reducing the filling volumes there will be a decrease in the pressure but not in the stroke volume.

These Figures (the right one for DHF and the left for SHF patients) show the correlation between end diastolic volumes (pressures) and stroke volume in heart failure patients. It teaches us that in heart failure patients the high pressures are not correlated with stroke volume (Cardiac output). Therefore if we will shunt a certain amount of blood away from the left ventricle we will not reduce the cardiac output both in DHF and SHF patients.

By designing a shunt which changes in flow capacity as a function of LAP, the shunt diameter can reduce to 3 mm when LAP is below 25 mmHg. Under such conditions, Q will be 0.35 l/min and the overall CO reduction is 0.35× 0.6/2=0.1 l/min in DHF and slightly less than 0.1 l/min in SHF (including compensation mechanisms).

Utilizing the parameters above to design a shunt ensures that during onset of Pulmonary Edema (PE), the shunt will open to 4 mm-5.5 mm and decrease LAP by 3 mmHg-5 mmHg. LA to RA flow will be 0.75 l·min-1 l/min. Under non-PE conditions, the shunt will remain patent just in the Atria's V-Wave and although the opening will be maximal it will only be for a short duration of 150 ms. As a result, LA-RA flow will be 0.3 l/min. the CO reduction will be less than 0.1 l/min Example 2

Construction and Deployment of One Embodiment of the Present Device

A device similar to the one illustrated in FIGS. 1A-2B is manufactured as follows. A NITINOL tube having a diameter of 5 mm, a length of 18 mm and a wall thickness of 0.25 mm is laser cut to create a tubular wire frame. The tubular frame is electro-polished and cleaned and then heat treated to set its final shape on a mandrel. The internal and external surfaces of the frame are wrapped with ePTFE. Valve leaflets are die cut from 0.25 mm thick bovine pericardium tissue and sutured to form a partially open leaflet valve which is then sutured onto the tubular frame over the fabric at the funnel opening. The resultant device is packed until use under sterile conditions. Prior to transplantation, the device is unpacked and collapsed by hand or by a crimping tool to a final diameter of less than 13 F. the collapsed device is loaded into a catheter and placed in front of a pusher rod fitted into the catheter. The device is then positioned as described hereinabove.

Example 3

Construction and Testing of a Diabolo-Shaped Device

Figure 6A:
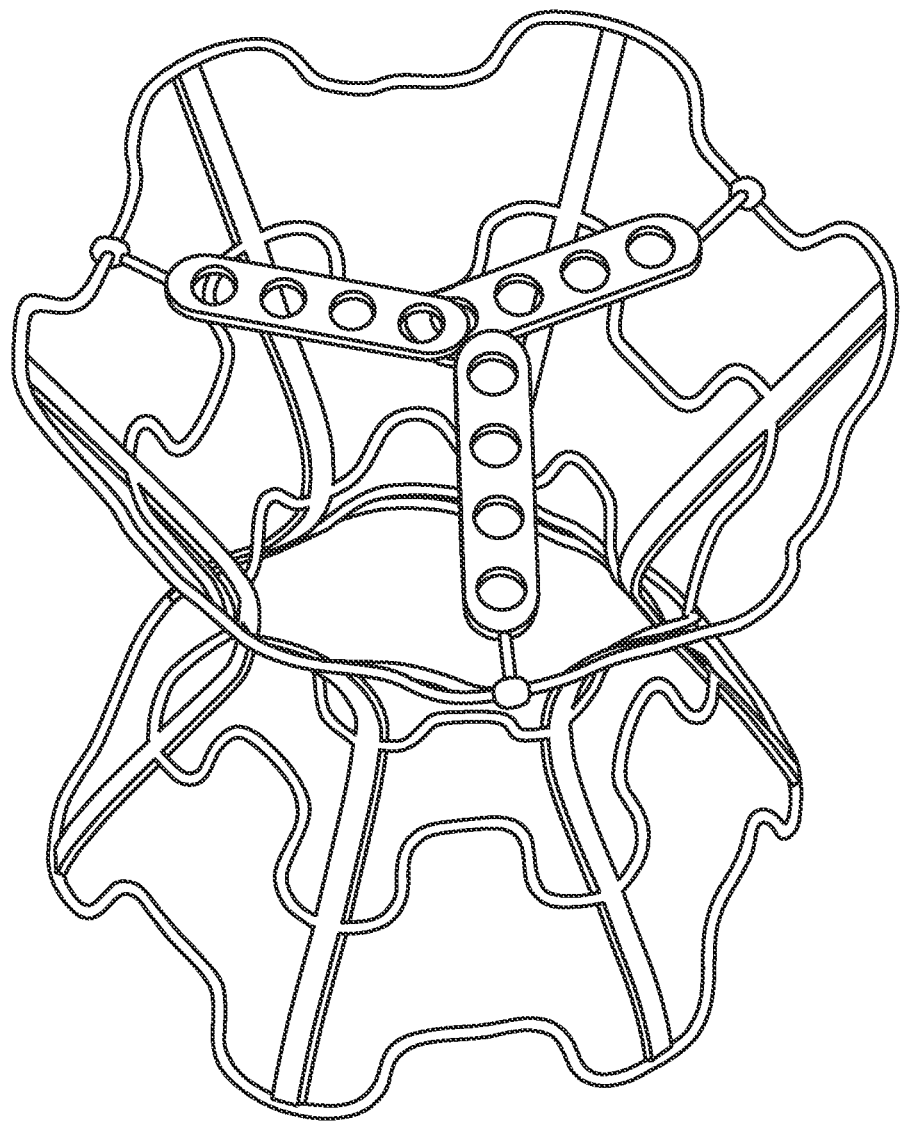
FIGS. 6A-6B illustrate the diabolo-shaped device of the present invention as a bare wire frame (FIG. 6A) and a PTFE/Pericard-covered wire frame (FIG. 6B).

A diabolo-shaped configuration of the present device was constructed by laser cutting a stent from Nitinol tubing and shaping the cut stent into a Diabolo by using a mandrel and applying 530° C. for 12 minutes. Bars for forming the valve arms were laser cut from a 0.0.09 mm thick Nitinol sheet and the bars were shaped using a mandrel. The shaped bars were then welded to the diabolo-shaped stent at three points encircling an opening of the stent. The bare wire frame form of the device is shown in FIG. 6A.

Figure 6B:

The stent was then covered with ePTFE impregnated with carbon and Pericard leaflets were sutured to the three bars and the circumference of the stent around the three bars (FIG. 6B). The finished device was then sterilized and collapsed for loading into a sheath.

The device shown in FIG. 6B was tested using the flow chamber described below to simulate the fluid pressures present in heart chambers. The device performed as specified i.e. when the valve was subjected to water pressure equivalent to a column of water>10 cm, the valve arms flexed inward and the valve opened to allow water flow at 0.5 l/min. Water pressure equivalent to a column of water<10 cm did not open the valve and thus did not result in any net water flow through the conduit (shunt) of the device.

Example 4

Leaflet Angle and Flow as a Function of Pressure Differentials

Figure 9A:
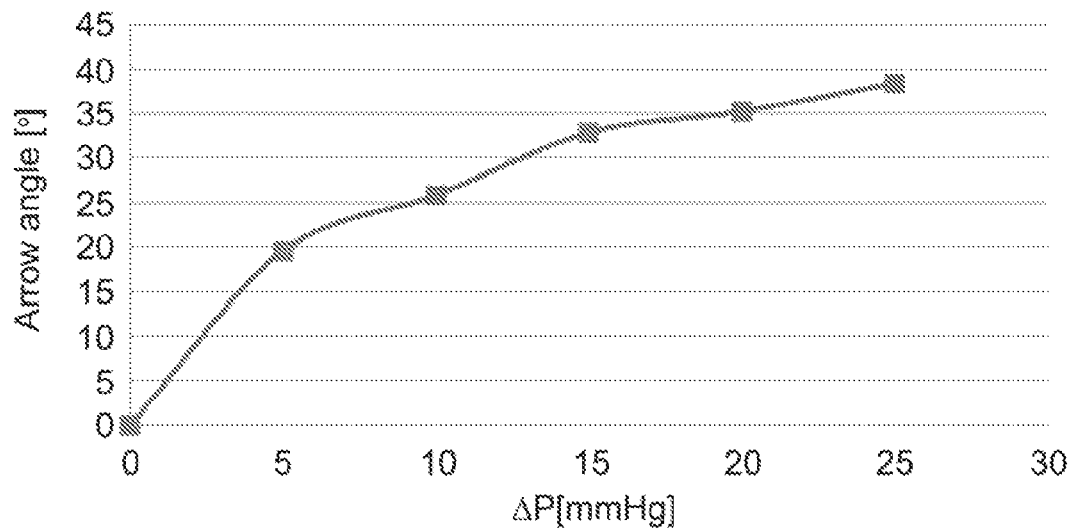
FIGS. 9A-9B illustrate the effect of a left atrium-right atrium pressure differential on leaflet opening angle (FIG. 9A) and flow rate (FIG. 9B).
Figure 9B:
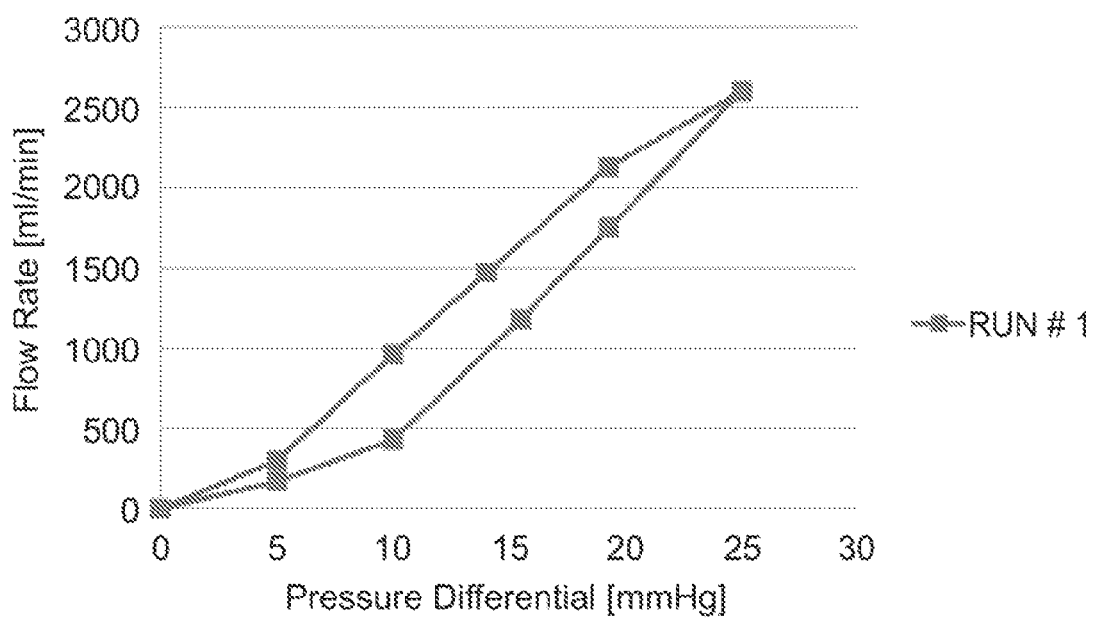

The present device was subjected to several pressure differentials using a flow chamber. Briefly, a two chambered device mimicking the left and right atria was constructed from plate Plexiglas. The device was positioned through a membrane separating the two chambers and water was pumped into the left chamber to generate a pressure gradient between the left and right chambers. Once the valve opened under the pressure of the water in the left chamber, water flowed into the right chamber and the flow rate was measured via a flow meter positioned on an output line connected to the bottom of the right chamber. The leaflet angle was determined by photographing the valve under the different pressure gradient conditions. Flow rates and leaflet angles were measured at several different pressure points from a first pressure at which the valve initially opens to a final pressure at which the valve was fully open. Leaflet angle and flow values obtained from six pressure differentials points were used to plot graphs (FIGS. 9A-9B).

Table 2 below exemplifies calculations of the leaflet angle at a 25 mmHg pressure differential.

TABLE 2

|  | X | Y |  | % of Diameter | % of original Length |  |
|---|---|---|---|---|---|---|
| Diameter | 6.24 | 1.09 | 6.334485 | 100 |  | angle |
| Arrow1 | 1.4 | 1.09 | 1.774289 | 28.00999 | 0.819125 | 35.00266 |
| Arrow2 | 1.14 | 0.37 | 1.198541 | 18.92089 | 0.738749 | 42.37504 |
| Arrow3 | 0.66 | 1.43 | 1.57496 | 24.86327 | 0.791299 | 37.69297 |
|  |  |  |  |  |  | 38.35689 |

As is shown by the FIGS. 9A-9B, a specific pressure differential (ΔP) can be correlated to a leaflet angle and a flow rate range.

Using the graph of FIG. 9A, a physician imaging the present device can convert an observed leaflet angle to a pressure differential. Alternatively, using the graph of FIG. 9B, a physician can translate an observed flow rate into a pressure differential. If desired, both graphs can be used to translate a leaflet angle to a flow rate and vise versa.

Therefore determining the leaflets angle or flow rate via, for example, imaging can provide a physician with an indication of pressure differential and as a result the pressure in the left atrium at any point in the heart cycle.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed:

1. A shunt for regulating blood pressure between a patient's left atrium and right atrium, the shunt comprising:
   a diabolo-shaped stent having a length greater than a thickness of the patient's atrial septum and comprising at least five sinusoidal rings interconnected by struts, the sinusoidal rings and struts defining a neck and first and second conical sections, the neck being adaptable to engage the atrial septum, the first and second conical sections being adaptable to protrude respectively into the left and right atria without contacting the atrial septum other than in a vicinity of the neck, the stent being configured to transition between a collapsed state suitable for percutaneous delivery and an expanded state when deployed across the patient's atrial septum.

2. The shunt of claim 1, wherein a flow rate capacity of the shunt increases with an increase in pressure of the left atrium.

3. The shunt of claim 1, wherein the stent is coated with expanded-polytetrafluoroethylene (ePTFE).

4. The shunt of claim 1, wherein the neck is between 4 and 6 mm in diameter.

5. The shunt of claim 1, wherein the neck has a length and a diameter, the neck length being greater than the thickness of the atrial septum.

6. The shunt of claim 1, wherein the length of the stent is greater than twice the thickness of the atrial septum.

7. The shunt of claim 1, wherein the stent is between 10 and 18 mm in length in the collapsed state.

8. The shunt of claim 1, wherein one of the at least five sinusoidal rings is located at the neck and has a diameter smaller than at least one other sinusoidal rings of the at least five sinusoidal rings.

9. A method of regulating blood pressure between a patient's left atrium and right atrium, the method comprising:
   deploying a device in a hole in the patient's atrial septum, the device comprising a diabolo-shaped stent having a length greater than a thickness of the patient's atrial septum and comprising a plurality of rings interconnected by struts, the rings and struts defining a neck and first and second conical sections, the neck being adaptable to engage the atrial septum, the first and second conical sections being adaptable to protrude respectively into the left and right atria without contacting the atrial septum other than in a vicinity of the neck, the stent being configured to transition between a collapsed state suitable for percutaneous delivery and an expanded state when deployed across the patient's atrial septum.

10. The method of claim 9, wherein the neck is between 4 and 6 mm in diameter.

11. The method of claim 9, wherein a flow rate capacity of the shunt increases with an increase in pressure of the left atrium.

12. The method of claim 9, wherein the stent is between 10 and 18 mm in length in the collapsed state.

13. The method of claim 9, wherein the plurality of rings are sinusoidal and the struts extend longitudinally.

14. The method of claim 9, wherein the stent is coated with expanded-polytetrafluoroethylene (ePTFE).

15. A shunt for regulating blood pressure between a patient's left atrium and right atrium, the shunt comprising:
a diabolo-shaped stent having a length greater than a thickness of the patient's atrial septum and comprising a plurality of rings interconnected by struts, the rings and struts defining a neck and first and second conical sections, the neck being adaptable to engage the atrial septum and being between 4 and 6 mm in diameter, the first and second conical sections being adaptable to protrude respectively into the left and right atria without contacting the atrial septum other than in a vicinity of the neck, the stent being configured to transition between a collapsed state suitable for percutaneous delivery and an expanded state when deployed across the patient's atrial septum.

16. The shunt of claim 15, wherein a flow rate capacity of the shunt increases with an increase in pressure of the left atrium.

17. The shunt of claim 15, wherein the plurality of rings are sinusoidal and the stent comprises at least five sinusoidal rings.

18. The shunt of claim 15, wherein the stent is coated with expanded-polytetrafluoroethylene (ePTFE).

19. The shunt of claim 15, wherein the neck has a length greater than the thickness of the atrial septum.

20. The shunt of claim 15, wherein the length of the stent is greater than twice the thickness of the atrial septum.

21. The shunt of claim 15, wherein the stent is between 10 and 18 mm in length in the collapsed state.

22. The shunt of claim 15, wherein one of the rings is located at the neck and has a diameter smaller than at least one of the other rings.

* * * * *